United States Patent
Tahan

(10) Patent No.: US 7,827,043 B2
(45) Date of Patent: Nov. 2, 2010

(54) METHOD USING A GLOBAL SERVER FOR PROVIDING PATIENT MEDICAL HISTORIES TO ASSIST IN THE DELIVERY OF EMERGENCY MEDICAL SERVICES

(76) Inventor: A. Christian Tahan, 1765 Northshore Rd., Suite 3, Revere, MA (US) 02151

( * ) Notice: Subject to any disclaimer, the term of this patent is extended or adjusted under 35 U.S.C. 154(b) by 777 days.

(21) Appl. No.: 09/784,751

(22) Filed: Feb. 15, 2001

(65) Prior Publication Data
US 2002/0111830 A1    Aug. 15, 2002

(51) Int. Cl.
    G06F 19/00    (2006.01)
    G06Q 10/00    (2006.01)
(52) U.S. Cl. .............................. 705/3; 705/2
(58) Field of Classification Search .......... 705/2–3; 600/300; 345/169; 283/66.1
    See application file for complete search history.

(56) References Cited

U.S. PATENT DOCUMENTS

| | | | | |
|---|---|---|---|---|
| 4,916,441 | A | * | 4/1990 | Gombrich .................. 345/169 |
| 5,822,544 | A | * | 10/1998 | Chaco et al. ................. 705/2 |
| 5,848,397 | A | | 12/1998 | Marsh et al. |
| 5,924,074 | A | * | 7/1999 | Evans ........................... 705/3 |
| 5,933,811 | A | | 8/1999 | Angles et al. |
| 5,948,061 | A | | 9/1999 | Merriman et al. |
| 5,974,398 | A | | 10/1999 | Hanson et al. |
| 5,992,890 | A | * | 11/1999 | Simcox ..................... 283/66.1 |
| 5,995,077 | A | * | 11/1999 | Wilcox et al. ............... 715/841 |

(Continued)

FOREIGN PATENT DOCUMENTS

WO    WO 99/44162    9/1999

(Continued)

OTHER PUBLICATIONS

Unknown. Internet Access : Free Web-Based Service Lets People Build and Maintain Their Personal Medical Records. Edge: Work-Group Computing Report, Jun. 8, 1998, vol. 8, No. 19, p. 3.

(Continued)

*Primary Examiner*—Robert W Morgan
(74) *Attorney, Agent, or Firm*—Robert K. Tendler

(57) ABSTRACT

An Internet based method for assisting in the rapid delivery of medical information direct to the site at which emergency assistance is being performed uses a global database for warehousing patient history information, which is fetched over the Internet on demand. In one embodiment, medical providers use an access code carried by the injured party and without which access is denied. The access code may be carried as a barcode and as an imprinted number on a bracelet or on a card carried by the individual. Patient information is transmitted over a network, either wireline or wireless, the Internet or wide area network, to a computer or personal digital assistant available to emergency personnel. In one embodiment, patient history information access is determined through the use of an access code reader, by entering the patient access code manually or by entering the patient's name as a last resort. Additionally insurance information can be made available to shorten emergency room admission procedures. Lastly, the patient's card or bracelet can allow for patient history to be downloaded and saved. Thus in emergency situations, the information can be uploaded from the card or bracelet to the healthcare providers' viewing screens.

9 Claims, 4 Drawing Sheets

U.S. PATENT DOCUMENTS

| | | | |
|---|---|---|---|
| 6,009,410 A | 12/1999 | Lemole et al. | |
| 6,398,727 B1* | 6/2002 | Bui et al. | 600/300 |
| 6,463,417 B1* | 10/2002 | Schoenberg | 705/2 |
| 2002/0004729 A1* | 1/2002 | Zak et al. | 705/3 |

FOREIGN PATENT DOCUMENTS

| | | |
|---|---|---|
| WO | WO 99 44162 A | 9/1999 |
| WO | WO 00/29983 | 5/2000 |
| WO | WO 00 29983 A | 5/2000 |

OTHER PUBLICATIONS

Kay, B. A. et al. Innovative Information-Sharing Strategies, Emerging Infections Diseases, Jul./Sep. 1998, vol. 4, No. 3, pp. 465-466.

Cook, B. Internet Train is Rolling. American Medical News. Oct. 4, 1999.

Borzo, G. Telemedicine: New Tools, Not New Medicine. American Medical News. Nov. 1, 1996, vol. 39, No. 42, pp. 55-57.

Guy, S. Conference Highlights Growing Reach of the Internet. American Medical News, Nov. 16, 1998, p. 27.

MEDICALRECORD.COM: Company Info. Printed on Dec. 29, 1999.

Unknown. MedicalRecord.Com Introduces Global Records Access and Management Tool System. Press Release. Aug. 24, 1999.

Newsom, M. Storing Medical Records A Healthy Web Use. Investors Business Daily. Nov. 3, 1998.

* cited by examiner

METHOD USING A GLOBAL SERVER FOR PROVIDING PATIENT MEDICAL HISTORIES TO ASSIST IN THE DELIVERY OF EMERGENCY MEDICAL SERVICES

FIELD OF INVENTION

This invention relates to the delivery of emergency medical services and more particularly to a method for providing patient medical history over the Internet.

BACKGROUND OF THE INVENTION

It will be appreciated that time is of the essence in the delivery of emergency services. As is well known, with a severed artery an individual can die within eight minutes. Moreover, there is a so-called "golden hour" in which if appropriate medical procedures are not administered, the likelihood of survival is substantially diminished.

In the past, a limited amount of medical history has been carried on bracelets worn by a stricken individual which at least instructs the EMTs or other emergency care professionals as to any allergic reactions that the individual may have. It can also alert to life threatening diseases such as AIDS so as to protect emergency personnel.

However, complete patient records have so far been unavailable to the emergency medical practitioner at the scene or at the point at which emergency help is administered. As a result, emergency medical personnel are at a great disadvantage when treating an individual in extremis.

There is therefore an urgent need to provide patient histories on the spot to assist medical providers in order to save lives or better render emergency assistance.

Such assistance would desirably be with the patient's consent, although ability to rapidly deliver patient records might take precedence over obtaining consent. Consent may however, play an important role.

As is usual, much of the patient's medical history is kept as a private record by his or her physician, by his or her hospital, or by his or her insurance company. Privacy issues surrounding the release of this information have in general resulted in large and unacceptable delays in getting this information to the primary healthcare provider. The results have been that people in emergency situations are denied the benefits of providing up-to-date information when trying to obtain treatment. Thus not only is patient history unavailable, such information when it becomes available, is available much later in the process.

Thus, delays in disseminating patient information are the result of privacy concerns, and for this reason patient information is not routinely transmitted anywhere outside a hospital environment, much less over the Internet. Moreover, present systems deny the patient the ability to consent to the transfer of the records to the appropriate healthcare provider under any circumstances. For this reason the individual has no choice in the matter and if unconscious is unable to give such consent in cases of emergency.

SUMMARY OF THE INVENTION

In the subject system, a global database is provided at a server linked via the Internet or other means to the site at which emergency assistance is rendered. The global database has access to the patient's medical history, and optionally insurance information, which is warehoused at one location. This information is instantly transmitted over the Internet to either a computer in an emergency room, to a rescue vehicle, or to a personal digital assistant carried by emergency personnel. The result is instant access to patient histories whenever it is needed.

If privacy is an issue, access to the information over the Internet is authorized, in one embodiment by a user ID or password, which can be a barcode and an imprinted number on a bracelet or a card within one's wallet. Alternatively, manual entry of the patient's access code precludes the necessity of access code readers.

In a preferred embodiment, each emergency health care provider is provided with a scanner which accesses the password or ID and transmits this password or ID to the global database server. The global database server then downloads or fetches the information over the Internet to the health care provider at the scene so as to permit the health care provider to make intelligent decisions about the treatment of the stricken individual.

In one embodiment, medical information can be entered at the scene using a data form provided for the purpose that can be e-mailed to the hospital before arrival, and is transmitted back to the global database server for storage.

For those situations in which privacy is an issue, in one embodiment of the subject invention, it is only by virtue of the consent of each individual that his or her information is provided to the emergency health care provider. Moreover, the individual may, at his election, wish to divulge only a certain portion of his medical history, which can be encoded and honored at the global database server.

While it may be unwise for a particular individual to limit the information seen by the emergency medical technician or physician, if such restricted access will cause the individual to give his or her consent, then the net benefit is still positive. Alternatively, the operator of the global database server may upon receipt of a request for restricting information contact the individual and discuss what information would be more appropriate and what information might be restricted. The simplest method is the organization of information by patient visit date (PDFs). Thus, the patient can indicate what date he or she does not want posted.

It will be appreciated that as part of the subject invention, it is possible for the global database server to be in the form of a number of networked database servers, with each server in each location acting as a regional server for that specific area. This prevents backlogs and provides realtime access to the information.

What is provided is on-the-spot access to patient medical information over a globally networked system. This allows for easier access to medical and insurance information, which in turn allows time to be saved and complete information to be received. The subject system saves time in emergency situations especially in emergency rooms or at the rescue scene and provides complete information for health care providers, particularly if the patient is unconscious. Because the information is accessible over the Internet, patient information can be accessed from any global location quickly, particularly because of the use of servers in various global locations. Moreover, any network medium including a computer, a handheld device such as personal digital assistant or any type of display linked to the network may be utilized. If the device to which the information is downloaded includes a wireless transmission such as a cell phone, then EMT practitioners or other medical professionals can have the additional benefit of e-mailing information or prescriptions to colleagues or pharmacies from the same screen.

As can be seen, what is provided is a centralized healthcare network connected to the far reaches of the world to assist emergency care by providing realtime access to patient histories to assist emergency care providers.

In summary, an Internet based method for assisting in the rapid delivery of medical information direct to the site at which emergency assistance is being performed uses a global database for warehousing patient history information, which is fetched over the Internet on demand. In one embodiment, medical providers use an access code carried by the injured party and without which access is denied. The access code may be carried as a barcode and as an imprinted number on a bracelet or on a card carried by the individual. Patient information is transmitted over a network, either wireline or wireless, the Internet or wide area network, to a computer or personal digital assistant available to emergency personnel. In one embodiment, patient history information access is determined through the use of an access code reader, by entering the patient access code manually or by entering the patient's name as a last resort. Additionally insurance information can be made available to shorten emergency room admission procedures.

Lastly, the patient's card or bracelet can allow for patient history to be downloaded and saved. Thus in emergency situations, the information can be uploaded from the card or bracelet to the healthcare providers' viewing screens.

BRIEF DESCRIPTION OF THE DRAWINGS

These and other features of the subject invention will be better understood in connection with the Detailed Description in conjunction with the Drawing of which.

DETAILED DESCRIPTION

It will be noted while the illustrated embodiment is described in terms of access codes, in the general case the subject invention involves the realtime Internet transfer of patient histories.

Figure 1:
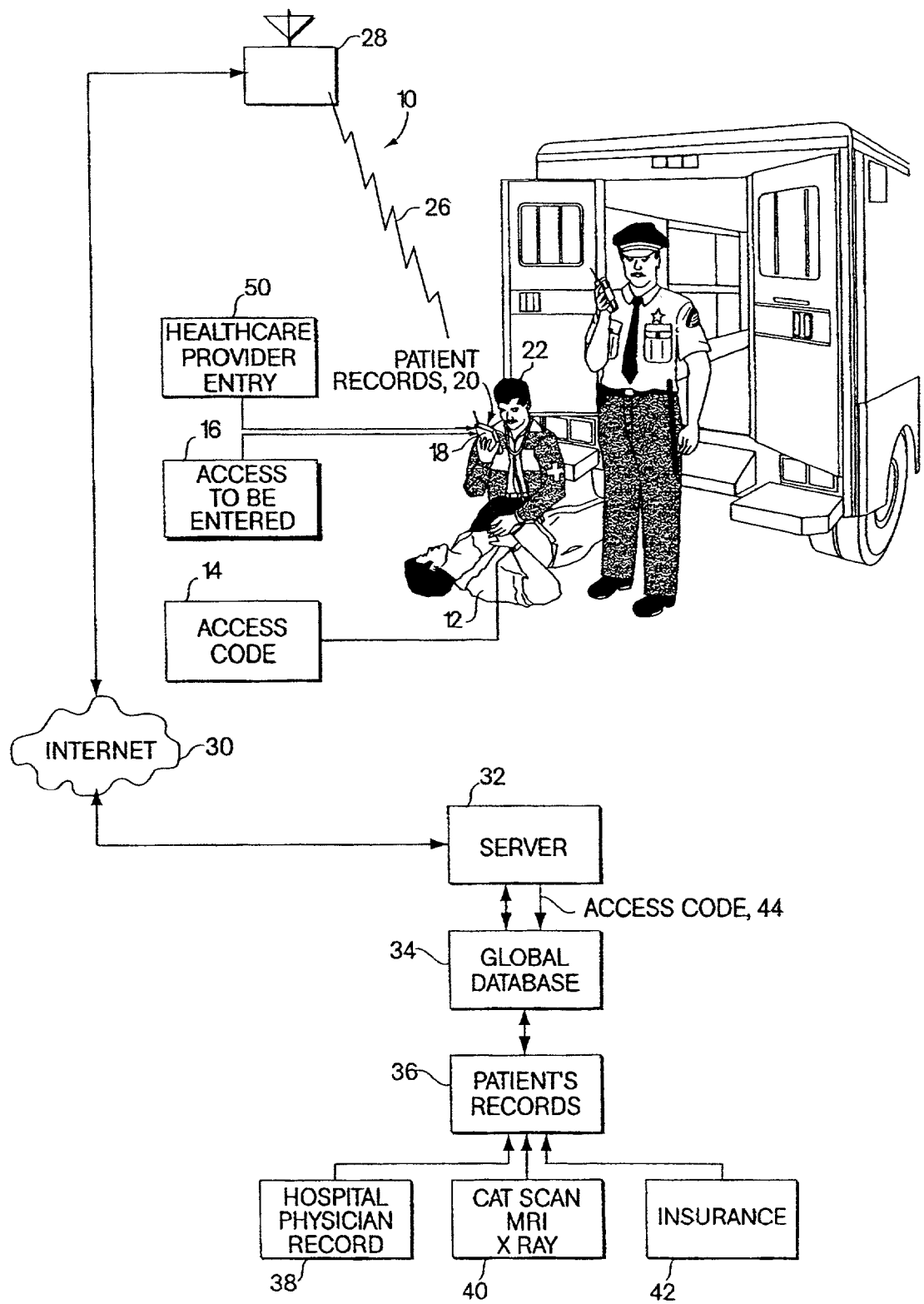
FIG. 1 is a diagrammatic representation of the subject system in which a healthcare professional attending an injured party is provided with the patient's record through the utilization of the Internet and a global database coupled to an Internet server.

With this understanding and referring now to FIG. 1, a system 10 includes an injured party 12, an access code providing device 14 which is read by an access code entry device 16, which in one embodiment can scan the access code from, for instance, a barcode carried by a bracelet or a card carried in the individual's wallet. Access code entry can also be done manually through a keypad or by whatever means is required in order to ascertain the access code associated with the injured party.

The access code is entered into a computer 18, which in the illustrated embodiment is a personal digital assistant having a screen at which a patient record 20 is accessible.

A healthcare professional, here illustrated at 22, is shown attending injured party 12 and is utilizing patient records 20 to determine the particular procedures to be utilized in the treatment of the injured party.

The information on this screen is provided, in the illustrated embodiment, over an RF link 26 to a cell tower 28 which is connected to the Internet 30 and thence to a server 32 which is turn connected to a global database 34. The global database is provided with the patient records here illustrated at 36 which can be composed of hospital/physician records 38, CT scans, NMRIs, X-rays 40, charts and graphs and optionally insurance data 42.

In operation, the healthcare professional, here illustrated at 22, ascertains the access code from the injured party and enters the access code through the local computer 18 which is then transmitted over the Internet to a server 32. Server 32 determines access, here illustrated at 44, and accesses database 34 with this access code to provide information from server 32 through Internet 30, cellsite 28 and RF link 26 to computer 18.

What is provided is an onsite patient record which is authorized by the utilization of the patient's access code carried by him or her. In this manner, the patient gives actual consent to the accessing of his or her patient records by virtue of carrying the access code on his or her person. In one embodiment, no access is permitted to the patient records without the injured parties actual consent. This actual consent is achieved through the provision of an access code to the individual and by virtue of the access code having been pre-coded into the global database.

If the patient is unconscious, then the permission to access his or her patient's record is automatic through access code entry by the healthcare provider or other professional.

It will be appreciated that in the illustrated embodiment there is no access to the patient's records absent his explicit consent as denoted by the carrying of the card or other device carrying his or her access code.

Optionally, as illustrated at entry device 50, those on the scene can enter data and transmit it back through the Internet and into the global database to modify the patient record in terms of care and other matters deemed pertinent by the healthcare provider at the scene. Also, computer 18 can be utilized to transmit prescriptions and other data needed elsewhere through the transmission path here established by RF link 26.

It will be appreciated that while the subject system is illustrated as being a wireless system, a hardwired system such as a computer in an emergency room is within the scope of this invention.

What is therefore provided is rapid access to authorized patient information which is useful both in the care of the injured party and in ascertaining the insurance qualifications of the individual, if such is necessary. The two-way communication link in which the patient record is an intrigal part is utilized, in one embodiment, to permit the forwarding of this information to further agencies such as a pharmacy or other experts so that prompt and accurate diagnosis can be made of the patient condition along with an appropriate treatment regimen.

Figure 2:
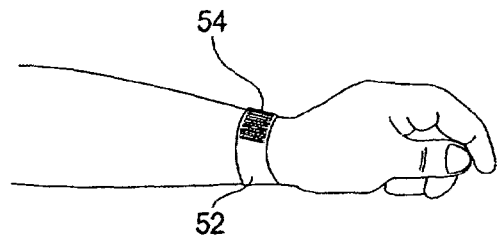
FIG. 2 is diagrammatic illustration of an access code entry system in which the access code is carried on a bracelet.

Referring now to FIG. 2, one way of providing an access code is by virtue of a bracelet 52 which has an access code 54 imprinted thereon, in one embodiment as a barcode. Other types of access code indication such as magnetic stripes in internally carried magnetic elements or color-coding may be utilized in the generation of the access code.

Figure 3:
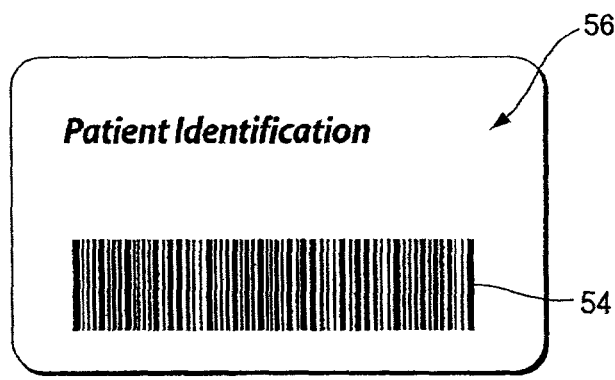
FIG. 3 is a diagrammatic representation of an access code entry system in which the access code is carried on a card carried by an individual.

Referring to FIG. 3, the same type of information can be encoded onto a card 56 in whatever manner as is convenient as in the case of the bracelet of FIG. 2.

Figure 4:
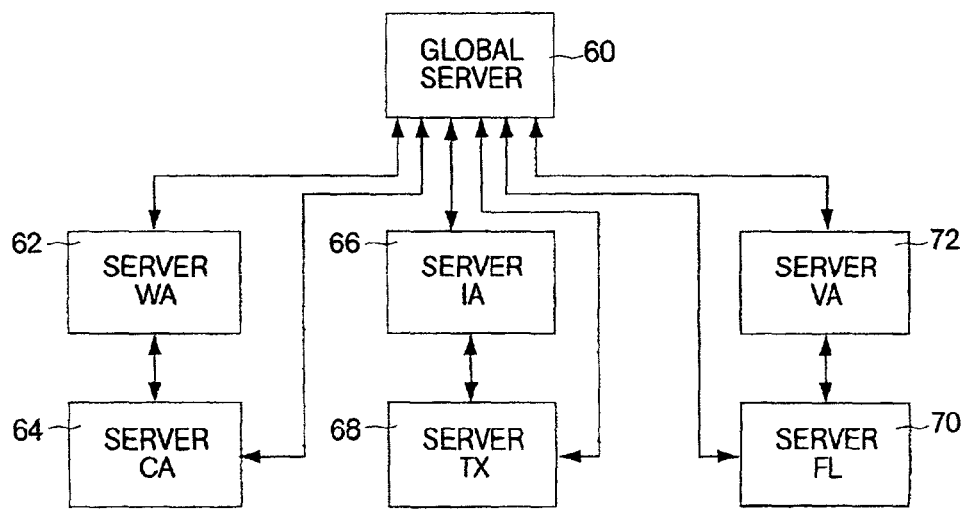
FIG. 4 is a block diagram of a global server coupled to regional servers to permit realtime data processing to provide the patient's record at the injured party.

Referring to FIG. 4, and as is described hereinbefore, a global server 60 may be coupled via the Internet or other means to regional servers 62, 64, 66, 68, 70 and 72. Such a global hosting system is described in U.S. Pat. No. 6,108,703 issued to F. Thomson Leighton et al. on Aug. 22, 2000. The purpose is to be able to transfer the centrally-generated information to local servers to reduce the time to transfer certain documents. This is particularly useful when the documents are not merely text but rather include images such as X-rays, CT scans, NMRIs or other pictorial data which must be used in the generation of a treatment regimen for the injured party. In the case illustrated, the servers may be as far as Washington state or Virginia and may be grouped as is convenient for the transmission of the patient information.

Figure 5:
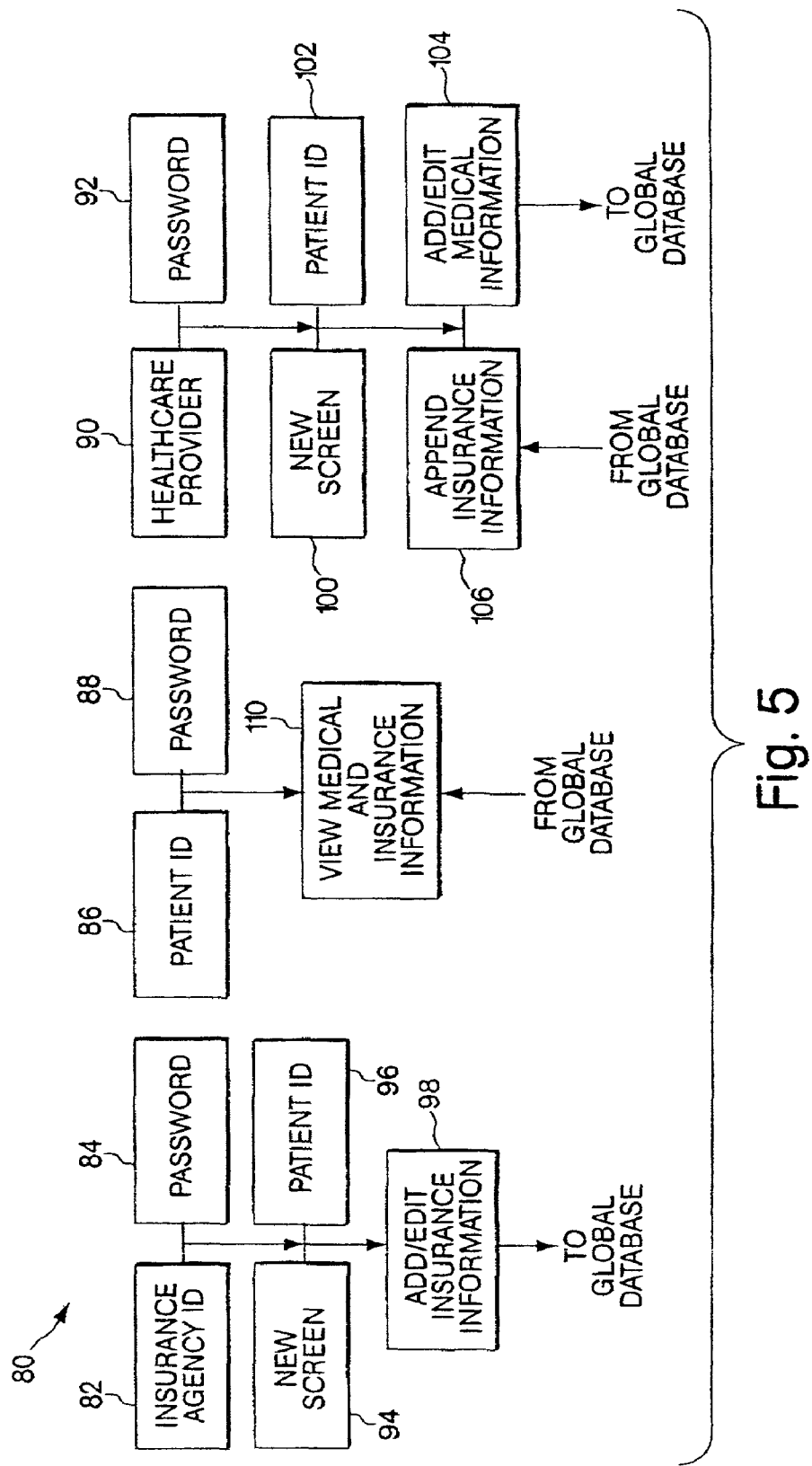
FIG. 5 is a diagrammatic illustration of a data entry structure including an initial web page in which the insurance agencies and healthcare providers can provide input to the global database, and in which the patient and/or those surrounding him can view the medical and insurance information from the global database; and, FIG. 6, is a flow chart of one embodiment of the subject invention.

Referring now to FIG. 5, a data entry structure is shown as an initial web page 80 which includes from left to right an insurance agency ID 82, a particular password or access code 84, a patient ID such as the patient name 86, a password or access code 88, a healthcare provider 90 and an access code 92.

From the insurance agency's point of view the insurance agency may wish to access patient information, here illustrated at a new screen 94, in accordance with the patient ID 96 and may choose to add or edit insurance information as illustrated at 98 which is then passed to the global database.

Likewise, healthcare provider 90 with the appropriate password or access code can be provided with a new screen 100 and a patient ID 102 to add or edit medical information to the global database as illustrated at 104, with appended insurance information as illustrated at 106 garnered from the global database.

Finally, the patient may be able to view his or her medical and insurance information by entry of a patient ID and a password or access code so that the entire record may be viewable to the patient as illustrated at 110 which information comes from the global database. Thus, the patient can monitor his or her treatment.

Figure 6:
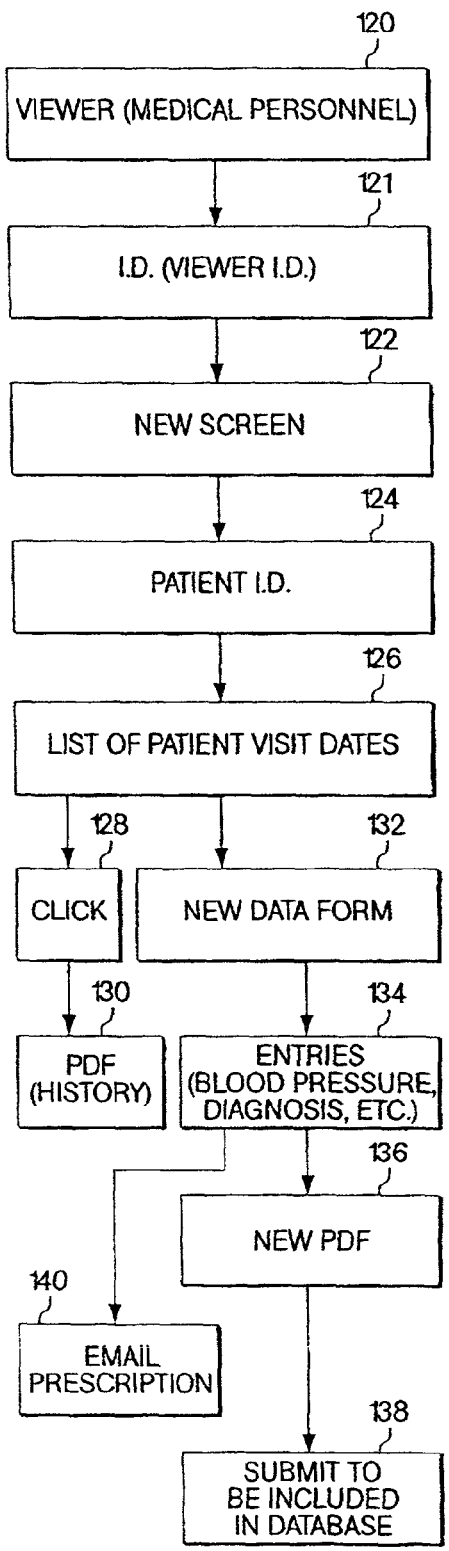

Referring now to FIG. 6, one of the best ways to provide patient histories is by saving the medical information as a PDF file. In the global database the newest entry is stored in one instance in a data form which is stored as a new PDF file.

Having this type of information available, the information may be provided over the Internet by providing a specialized web page for each patient. As can be seen from FIG. 6, a viewer 120 may be using a viewer ID 120 to access a new screen 122 which upon receipt of the patient ID 124 provides a list of patient dates 126. These are then clicked at 128 to provide a PDF history 130 presented over the Internet.

New entries are provided by the new entry data form 132 which provides entries 134 such as blood pressure, diagnostic data and charts or graphs which result in a new PDF 136 being generated. This is submitted to be included on the database as illustrated at 138.

Additionally, e-mail prescriptions can be provided over the Internet from the entries at 134 as illustrated at 140.

While there are many methods to transmit data from a hospital or doctors office, in one embodiment the patient records, if saved on database, can be e-mailed and then converted to a PDF file at the global database.

On the other hand, the patient records at the hospital or doctor's office can be scanned and e-mailed to the global database where they are converted to PDF files. In this manner, regardless of the form in which patient records are kept, they can be provided in a PDF format by merely scanning them and transmitting the PDF file via e-mail. As a result, they can be preserved in the database as a PDF or other type of file.

While the PDF modality has been described herein, it will be appreciated that any universal method may be applied to the transmission of data from a hospital or a doctor's office to the global database. Moreover, patient records may be transmitted to the ultimate user through a modality other than PDF files. If utilizing a universal format, PDF files need not be used. Rather, the electronic form in which the patient's record are kept may be used directly. The advantage of using PDF or like files is to be able to transmit to the ultimate recipient, namely the medical care provider, not only whatever handwritten records exist but also the signatures on these records, and also any X-Rays, NMR renderings or indeed charts of any kind, that need not be in a particular format in order to be transmitted to the end recipient.

Having now described a few embodiments of the invention and some modifications and variations thereto, it should be apparent to those skilled in the art that the foregoing is merely illustrative and not limiting, having been presented by the way of example only. Numerous modifications and other embodiments are within the scope of one of ordinary skill in the art and are contemplated as falling within the scope of the invention as limited only by the appended claims and equivalents thereto.

What is claimed is:

1. A method of providing patient histories to a site at the location of a patient in need of medical attention, comprising the steps of:
   providing patient histories at a centralized location in a global database coupled to the Internet by a server; and,
   wirelessly accessing a predetermined patient history over the Internet from a wireless terminal at said site and uploading patient information from said site.

2. The method of claim 1, wherein said patient history is only transmitted when authorized by the patient.

3. The method of claim 2, wherein authorization is in the form of an access code carried by the patient.

4. The method of claim 3, wherein said access code is obtained from the patient and is transmitted to the server associated with said global database.

5. The method of claim 4, wherein the access code is carried by the patient.

6. The method of claim 5, wherein the access code is in the form of a bar code and wherein a bar code reader is used to read the access code and transmit the access code to the server associated with said global database.

7. The method of claim 5, wherein the access code is carried on a bracelet.

8. The method of claim 5, wherein the access code is imprinted on a card adapted to be carried.

9. The method of claim 1, wherein said global database is decentralized through the use of regional databases, each having its own server and each carrying patient histories so that access to the patient history can be on a real time basis to permit timely treatment.

* * * * *